United States Patent
Hall et al.

(10) Patent No.: US 11,187,695 B2
(45) Date of Patent: Nov. 30, 2021

(54) METHOD OF USING AN ELECTRONIC CHEMICALLY SENSITIVE RESISTOR ARRAY FOR THE DIFFERENTIATION OF SYNTHETIC AND AUTHENTIC URINE SPECIMENS

(71) Applicants: David R. Hall, Provo, UT (US); Steven J. M. Butala, Provo, UT (US); Estanislado Bravo, Provo, UT (US); Joshua Larsen, Spanish Fork, UT (US)

(72) Inventors: David R. Hall, Provo, UT (US); Steven J. M. Butala, Provo, UT (US); Estanislado Bravo, Provo, UT (US); Joshua Larsen, Spanish Fork, UT (US)

(73) Assignee: Hall Labs LLC, Provo, UT (US)

( * ) Notice: Subject to any disclaimer, the term of this patent is extended or adjusted under 35 U.S.C. 154(b) by 299 days.

(21) Appl. No.: 16/132,918

(22) Filed: Sep. 17, 2018

(65) Prior Publication Data
US 2020/0088714 A1    Mar. 19, 2020

(51) Int. Cl.
*G01N 33/493* (2006.01)
*G01N 33/94* (2006.01)
*G01N 33/487* (2006.01)

(52) U.S. Cl.
CPC ..... *G01N 33/493* (2013.01); *G01N 33/48714* (2013.01); *G01N 33/94* (2013.01)

(58) Field of Classification Search
CPC .......... G01N 33/493; G01N 33/48707; G01N 33/48714; G01N 33/50; G01N 33/94; A61B 10/0045; A61B 10/007; A61B 5/4845

See application file for complete search history.

(56) References Cited

U.S. PATENT DOCUMENTS

| | | | |
|---|---|---|---|
| 2008/0204240 A1* | 8/2008 | Hilgers | G01D 21/00 340/572.1 |
| 2014/0023557 A1* | 1/2014 | Tian | G01N 33/0027 422/88 |
| 2017/0204595 A1* | 7/2017 | Hall | E03D 9/052 |

OTHER PUBLICATIONS

Sabeel et al ("Detection of volatile compounds in urine using an electronic nose instrument", 2013, International Conference on Computing, Electrical and Electronic Engineering ICCEEE, pp. 1-4 (Year: 2013).*

(Continued)

*Primary Examiner* — Benjamin R Whatley
*Assistant Examiner* — Austin Q Le

(57) ABSTRACT

The method uses a device which measures the volatile organic compounds (VOCs) present in headspaces of fluid samples to differentiate between authentic and synthetic urine samples. The method includes the use of a device which includes an array of resistive microchemical sensors. The device may be exposed to samples of synthetic and authentic urine to identify a pattern of VOCs in each, these steps being referred to herein as training the device. The device may then be exposed to a urine sample of unknown authenticity and a pattern of VOCs identified. The pattern of VOCs from the urine sample of unknown authenticity may be compared to those of synthetic and authentic urine. In some embodiments the device is installed in a toilet. The method may be used to identify a false sample provided for a urine analysis intended to screen for use of illicit drugs.

20 Claims, 4 Drawing Sheets

(56) References Cited

OTHER PUBLICATIONS

Quick Fix ("What's New In The Testing Industry?", https://web.archive.org/web/20170917054222/https://www.quickfixurine.com/ retrieved using wayback machine and published online on Aug. 26, 2017 (Year: 2017).*

Sensigent ("Cyranose Electronic Nose"; https://web.archive.org/web/20170826065623/http://www.sensigent.com/products/cyranose.html retrieved using wayback machine and published on Aug. 26, 2017 (Year: 2017).*

Catching Fakes: New Markers of Urine Sample Validity and Invalidity, Journal of Analytical Toxicology, vol. 41, Issue 2, pp. 121-126 (Year: 2017).*

\* cited by examiner

METHOD OF USING AN ELECTRONIC CHEMICALLY SENSITIVE RESISTOR ARRAY FOR THE DIFFERENTIATION OF SYNTHETIC AND AUTHENTIC URINE SPECIMENS

BACKGROUND

Field of the Invention

This disclosure relates to urine analysis, drug testing, and methods of providing inaccurate results in drug testing.

Background of the Invention

Commonly employed methods for obtaining fraudulent results of drug urinary tests include dilution of urine specimens by consuming copious amounts of water or flushing the body with herbal remedies. It has been reported the latter is ineffective and the former can be detected via creatinine and specific gravity measurements. Creatinine limits are set at 2-20 mg/dL and specific gravity is set at 1.003; urine outside of these specifications is classified as a "diluted specimen," Hence, there is an increased demand for synthetic urines that are balanced for pH, creatinine, and specific gravity making their detection difficult. A method is needed which quickly and easily determines the authenticity of a urine sample.

BRIEF SUMMARY OF THE INVENTION

We disclose a method for using an electronic nose to differentiate between authentic urine samples and synthetic urine. The method includes the use of an electronic volatile compound sensing device (hereinafter "electronic nose") which may include a vapor sampling system, an array of resistive microchemical sensors, and a controller. The array of resistive microchemical sensors may include metal oxide semiconductors, conducting polymers, piezoelectric sensors, metal oxide sensors, or combinations thereof. The controller may include nontransitory computer readable medium which stores at least one algorithm. The algorithm may include instructions for recognizing patterns in changes in resistance at each of the resistive microchemical sensors.

The method includes the steps of training the electronic nose to both authentic urine and synthetic urine. For each of authentic and synthetic urine samples, the electronic nose may be introduced to the headspace of the sample which include vapor. The vapor may include volatile organic compounds (hereinafter "VOCs") from the sample. The pattern of change in resistance of each of the resistive microchemical sensors in response to the vapor from each sample may be stored on the controller. The electronic nose may be purged between each sample reading. In some embodiments, each of the authentic and synthetic urine samples may be brought to physiological temperature prior to introducing the headspace to the electronic nose.

In some embodiments, a baseline measurement may be conducted. This may be accomplished by introducing the vapor sampling system to an air sample which does not include VOCs from a urine sample, authentic or synthetic. The air sample may include room air, the headspace of a container of water, or a headspace of a toilet bowl which includes toilet water. The baseline measurement may be used as a negative control or a background measurement with which to compare subsequent sample readings. The baseline measurement may be collected by performing a measurement of a change in resistance at each of the resistive microchemical sensors in the array in response to the air sample. The pattern of change in resistance of each of the resistive microchemical sensors in response to the air sample may be stored in the controller.

A urine sample of unknown authenticity may then be provided for analysis. The headspace of this sample may be analyzed using the electronic nose in the same manner as the samples used for training. In some embodiments, the urine sample of unknown authenticity may be within a physiological temperature range prior to sampling its headspace. A change in resistance at each of the resistive microchemical sensors in the array may be detected and these measurements stored on the controller.

A calculation may be performed to determine the $R_{max}/R_0$. $R_0$ represents the resistance measured by each of the resistive microchemical sensors in the array following the baseline draw. $R_{max}$ represents a maximum resistance measured by each of the resistive microchemical sensors in the array after introducing the device to the urine sample of unknown authenticity. In some embodiments, the method may include providing an output which communicates the analysis of the authenticity of the urine sample of unknown authenticity and the result of the calculation to determine $R_{max}/R_0$ as well as the results of calculations performed by other algorithms stored on the controller.

In some embodiments, the controller may include algorithms which conduct a statistical analysis of the analysis. In some embodiments, the controller stores algorithms which perform one or more of a multivariate statistical procedure, a k-nearest neighbors prediction probability routine, a k-means cluster analysis, a categorical data analysis, a soft independent modeling of class analogy analysis, a single-class analysis, a support vector machine analysis.

While in some embodiments the method includes an electronic nose which is a handheld device, in other embodiments, the electronic nose may be installed within a toilet. In some embodiments, the toilet is a medical toilet. In some embodiments, the toilet includes both a P-trap and a separate air pipe. In some embodiments, the toilet may include a fan which directs air from the headspace of the toilet bowl toward the electronic nose for analysis. The fan may be configured to direct air at a velocity which is optimal for analysis by the electronic nose. The toilet may include a valve which regulates the entry of air from the headspace of the toilet bowl into the air pipe.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings.

DETAILED DESCRIPTION OF THE INVENTION

Definitions

Figure 1A:
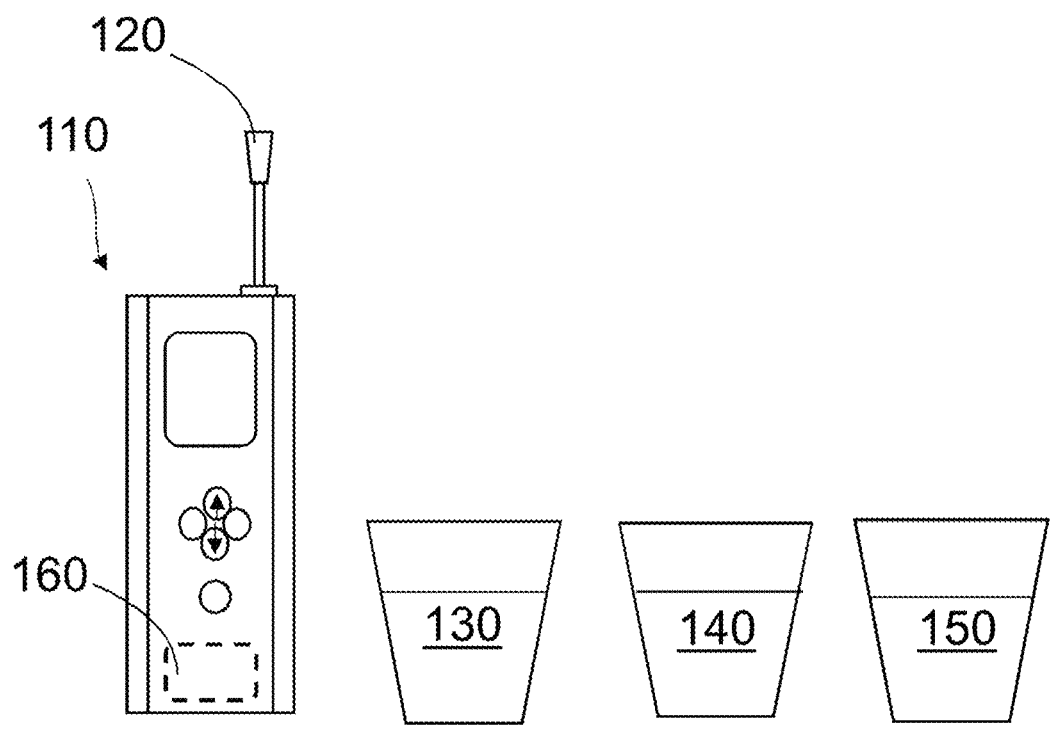
FIGS. 1A and 1B are plan views of a hand-held resistor array and urine samples, synthetic, authentic, and unknown.

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "medical toilet" means an apparatus for collecting human waste which also conducts physiological measurements during use, including, but not limited to, analysis of a user's urine.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a method to differentiate between authentic urine samples and synthetic urine samples using an electronic nose. In some embodiments, this method may be used to identify a synthetic urine sample provided to evade detection of drug use or to pass physical exams performed to confirm a person's health.

An electronic nose is a device designed to mimic the human olfactory system. It may include a vapor sampling system, a detection system, and a controller. The vapor sampling system may deliver a gaseous mixture to the detection system which usually includes an array of resistive microchemical sensors. The array may include between 20 and 100 resistive microchemical sensors, for example, 32 resistive microchemical sensors, or more. The resistive microchemical sensors may include a metal oxide semiconductor, conducting polymers, piezoelectric sensors, metal oxide sensors, or combinations thereof.

Because urine, whether authentic or synthetic, comprises mostly water, the hydroxyl-group-specific resistive microchemical sensors may be deactivated. This may prevent signal detections which are the result of the water in each sample. Failing to do so may result in readings which are mostly analyzing water, and which indicate little differences between the samples.

Signals detected by the microchemical sensors may then be processed by the controller which may include nontransitory computer readable medium. Instructions to apply machine learning classification algorithms which recognize patterns in the microchemical sensor signals may be stored on the nontransitory computer readable medium. These algorithms may include multivariate statistical procedures which may include, for example, principal component analysis (PCA). Other examples of machine learning classification algorithms which may be stored on the nontransitory computer readable medium include a k-nearest neighbors prediction probability routine, a k-means cluster analysis, a categorical data analysis, and a support vector machine analysis. The pattern of change in resistance of each of the resistive microchemical sensors in response to the vapor from each sample may be stored on the controller.

The method may include the steps of training the electronic nose to both authentic urine and synthetic urine. The training may include the step of introducing the electronic nose to the headspace of an authentic and a synthetic urine sample, each of which includes vapor. The vapor may include VOCs from the samples. The pattern of change in resistance of each of the resistive microchemical sensors in response to the vapor from each sample may be stored on the controller. In some embodiments, electronic nose may be trained to multiple different formulations of synthetic urine and multiple authentic urine samples.

In some embodiments, each of the authentic and synthetic urine samples may be brought to physiological temperature prior to introducing the headspace to the electronic nose. In some embodiments, the temperature may be adjusted by transferring the sample into a container which may be placed against a person's body. A heating device, for example, a handwarmer may be used to bring the sample to within a physiological temperature range. As disclosed in more detail elsewhere herein, the electronic nose may be installed within a toilet. In this embodiment, the toilet may include a heating device which adjusts the temperature of the authentic and synthetic urine samples after they are deposited in the toilet bowl. As defined herein, physiological temperature may be between approximately 97° F. and approximately 104° F. Clearly, a variety of heating devices may be used to bring the sample to within a physiological temperature range.

In some embodiments, electronic nose may be purged between each sample reading. This action may remove residual organic molecules which may linger from previous sample readings.

In some embodiments of the disclosed method, a baseline measurement may be conducted. The baseline measurement may be accomplished by introducing the vapor sampling system to an air sample which does not include VOCs from a urine sample, authentic or synthetic. The air sample may include room air, the headspace of a container of water, or a headspace of a toilet bowl which includes toilet water. The baseline measurement may be used as a negative control or a background measurement with which to compare subsequent sample readings. The baseline measurement may be collected by performing a measurement of a change in resistance at each of the resistive microchemical sensors in the array in response to the air sample. The pattern of change in resistance of each of the resistive microchemical sensors in response to the air sample may be stored in the controller. Baseline measurement readings may be used in calculations which subtract background readings from sample readings.

A urine sample of unknown authenticity may then be provided for analysis. In some embodiments, a plurality of samples of unknown authenticity may be analyzed. The headspace of the sample of unknown authenticity may be analyzed using the electronic nose in the same manner as the samples used for training. In some embodiments, the urine sample of unknown authenticity may be within a physiological temperature range prior to sampling its headspace using methods described above with regard to training the electronic nose to authentic and synthetic urine samples. A change in resistance at a plurality of the resistive microchemical sensors in the array may be detected and these measurements stored on the controller.

A calculation may be performed to determine the $R_{max}/R_0$. $R_0$ represents the resistance measured by each of the resistive microchemical sensors in the array following the baseline draw and $R_{max}$ represents a maximum resistance measured by each of the resistive microchemical sensors in the array after introducing the device to the urine sample of unknown authenticity.

In some embodiments, the method may include providing an output which communicates the analysis of the authenticity of the urine sample of unknown authenticity. The output may communicate the result of the calculation to determine $R_{max}/R_0$ as well as the results of calculations performed by other algorithms stored on the controller. In some embodiments, the output is a digital readout on a screen. The screen may be a part of the electronic nose, as when the electronic nose is a handheld device. The output may simply be an indication of authentic or synthetic urine, for example, lighting a green or a red light on the handheld electronic nose. In some embodiments, the output may be separate from the electronic nose. In embodiments in which the electronic nose is installed within a toilet, the output may be a screen or light connected to the toilet.

While in some embodiments the method includes an electronic nose which is a handheld device, in other embodiments, the electronic nose may be installed within a toilet. In some embodiments, the toilet is a medical toilet. The medical toilet may include additional sensors which collect a user's body weight, blood pressure, heart rate, breathing rate, collect bioimpedance measurements or combinations thereof.

In some embodiments, the toilet may include an exhaust system which directs air from the headspace of the toilet bowl toward the electronic nose for analysis. The exhaust system may include a fan. The fan may be configured to direct air from the headspace at a desired velocity which is optimal for analysis. In this embodiment, the fan may be in electrical connection with the controller which may modify the velocity of the air. In some embodiments, the exhaust system includes both a P-trap and a separate air pipe. The toilet may include a valve which regulates the entry of air from the headspace of the toilet bowl into the air pipe. In some embodiments, the toilet and exhaust system may be as disclosed in U.S. patent application Ser. No. 15/338,861 filed on Oct. 31, 2016, which is hereby incorporated by reference in its entirety. In some embodiments, the toilet includes a heating device. The heating device may be configured to adjust the temperature of the sample or air to be analyzed to a desired temperature. The desired temperature may be within a physiological temperature range. The heating device may be in electrical connection with the controller which may modify the temperature of the sample or air.

Referring now to the drawings, FIG. 1A shows sensing device 110. Sensing device 110 includes vapor intake 120 which is part of a vapor sampling system within sensing device 110. Sensing device 110 also includes an array of resistive microchemical sensors within and controller 160 which stores non-transitory computer readable medium. The non-transitory computer readable medium stores algorithms for processing the readings collected by the microchemical sensors. Three sample containers, each holding a liquid, are shown. Sample container 130 holds a known synthetic urine sample while sample container 140 holds a known authentic urine sample. Sample container 150 holds a urine sample of unknown authenticity.

Figure 1B:
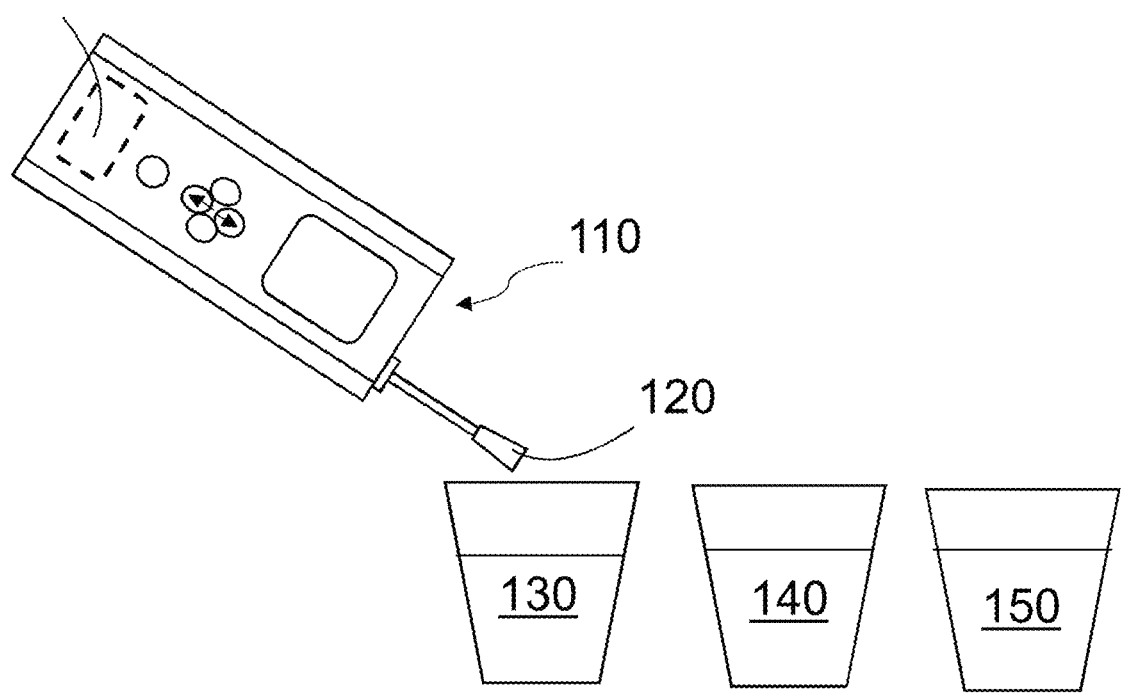

FIG. 1B illustrates the use of sensing device 110 in an embodiment of the disclosed method. Sensing device 110 is positioned such that vapor intake 120 is placed adjacent to the headspace of sample container 130. At this point, sensing device 110 is being trained on the synthetic urine sample in sample container 130. Sensing device 110 will next be trained on the authentic urine sample in sample container 140 as with sample container 130. By training sensing device 110 on the contents of sample containers 130 and 140, the microchemical sensor array detects the volatile organic compounds (VOCs) in their headspaces and stores the reading in controller 160. Finally, sensing device 110 will sample the urine sample of unknown authenticity in sample container 150 by sampling the headspace as shown with sample container 130. The microchemical sensor array will collect a reading of the VOCs in the headspace of container 150 and controller 160 will compare the reading with those stored for the contents of containers 130 and 140. Controller 160 within sensing device 110 will provide an analysis of the authenticity of the urine sample in sample container 150 by determining if its VOC profile most resembles that of the contents of container 130 or container 140.

Figure 2A:
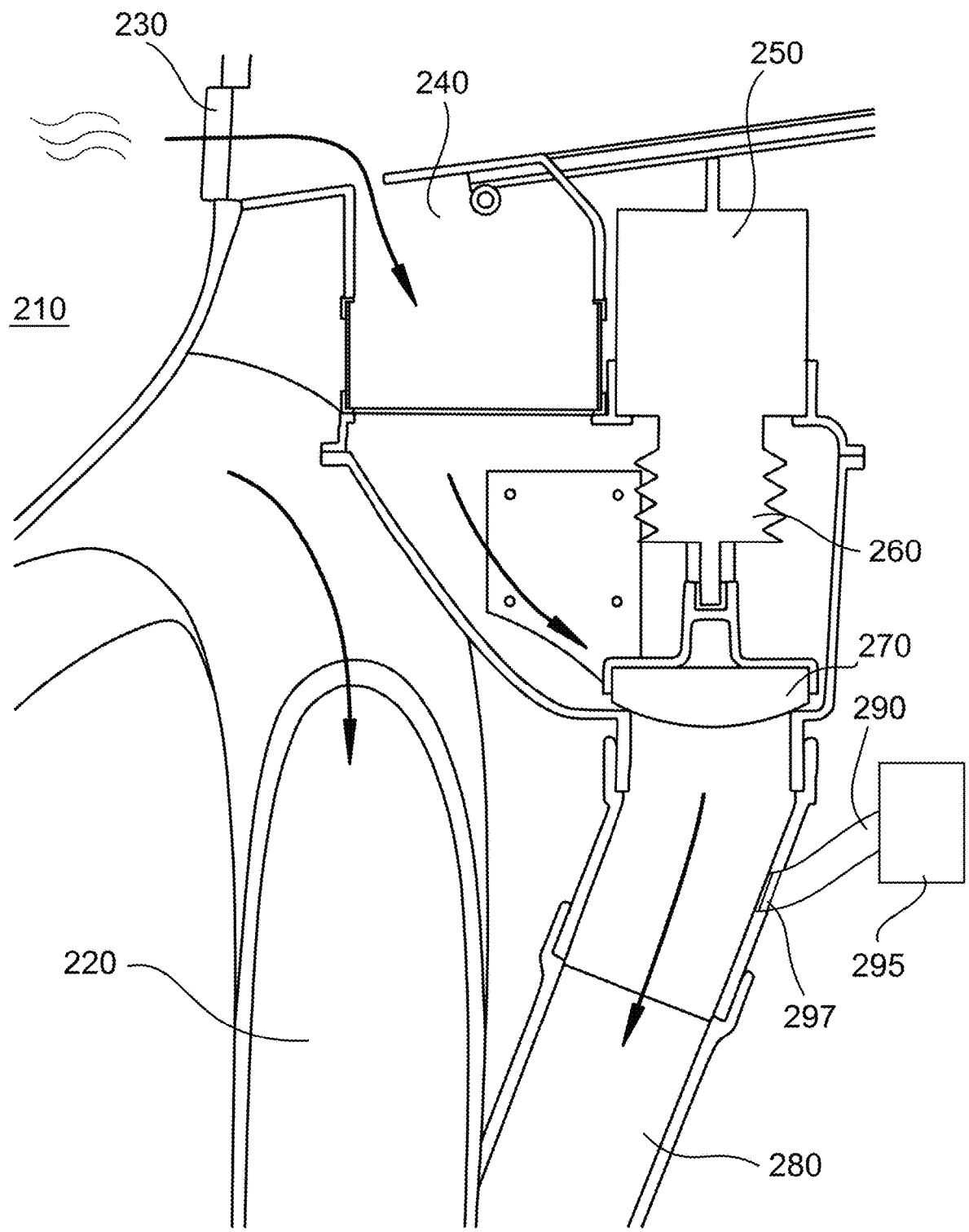
FIG. 2A is a cross-sectional perspective drawing illustrating an air handling system within a toilet including a resistor array.

FIG. 2A is a close-up of an air sampling system which is housed within a toilet. The air sampling system analyzes volatile compounds from the headspace of a toilet bowl using an electronic nose. The embodiment shown is an exhaust system as shown in U.S. patent application Ser. No. 15/338,861 filed on Oct. 31, 2016, which is hereby incorporated by reference in its entirety. The system includes a bifurcated manifold which includes P-trap 220 for transporting waste from toilet bowl 210 into the sewer system. It also includes air pipe 280 for transporting air from the headspace of toilet bowl 210 for analysis using the electronic nose. According to the disclosed method, a user deposits bodily waste into toilet bowl 210. The user flushes the toilet and the waste travels into P-trap 220 leading to the sewer system. Air vent 230 leads from toilet bowl 210 into air pipe 280. Air pipe 280 connects air vent 230 with an output port that leads into the sewer pipe. Accordingly, the air eventually joins the waste transported by P-trap 220. Fan 240 is located within air pipe 280 and, when actuated, draws air from toilet bowl 210, through air vent 230, and into air pipe 280. Wavy lines shown within toilet bowl 210 represent air moving toward air vent 230 and arrows moving from air vent 230 through air pipe 280 indicate the direction of air movement.

Piston 270, solenoid 260, and base 250 form a valve. When the valve is open (piston 270 is raised), fan 240 directs air from the headspace of toilet bowl 210 into air pipe 280. Some of the air enters conduit 290 and into sensing device 295 which includes an array of resistive microchemical sensors as discussed elsewhere herein. Consequently, sensing device 295 samples and identifies the mix of VOCs in a urine sample.

Concentrator 297 is shown in connection with conduit 290. Concentrator 297 may be present in some embodiments because the VOCs to be analyzed may be diluted after the urine sample reaches the toilet. For example, the toilet water, the air in the headspace, or both may dilute the VOCs to a concentration which is below that which is optimal for analysis. Concentrator 297 may include a plurality of membranes through which the VOCs may pass, each concentrating the VOCs to a greater extent. Concentrator 297 may also include a membrane which prevents toilet water from entering conduit 290 which may damage sensing device 295.

Figure 2B:
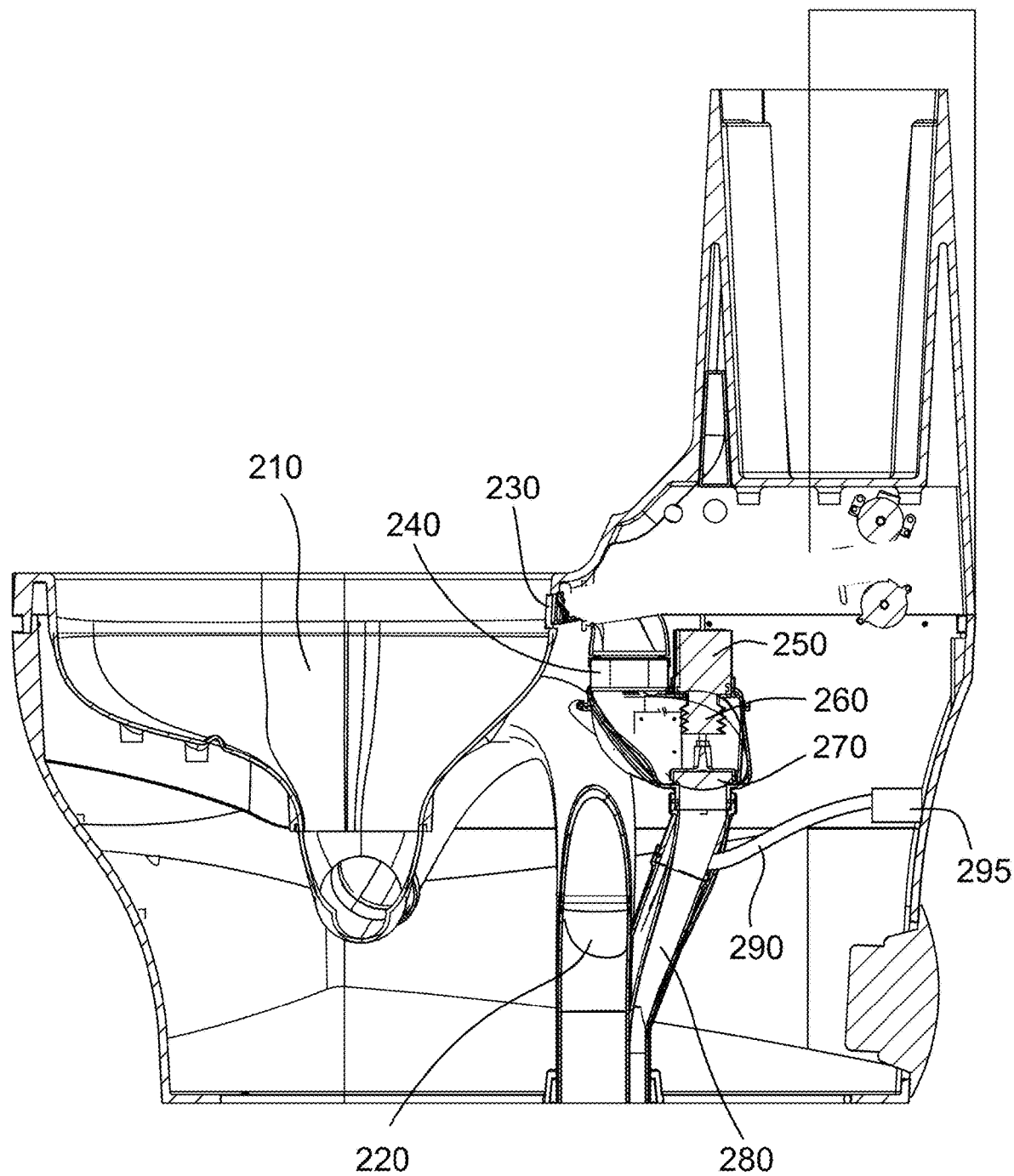
FIG. 2B is a cross-sectional perspective drawing which is an expanded view of the toilet housing the air handling system of FIG. 2A.

FIG. 2B is an expanded view of the air sampling system of FIG. 2A in which more of the toilet is visible. When piston 270 is raised, air travels from the headspace in toilet bowl 210, through the air handling system as described above with regard to FIG. 2A, is concentrated by concentrator 297, and reaches sensing device 295 for analysis. P-trap 220 and air pipe 280 then join to dispense their contents into a sewer system.

EXAMPLES

Materials and Methods:

The electronic volatile compound sensing device, hereinafter, "electronic nose," utilized for our experiments was the Cyranose® 320 from Sensigent (Baldwin Park, Calif.). The Cyranose® 320 is a handheld device which includes a 32 nanocomposite sensor array of resistive microchemical sensors, a vapor sampling conduit, and a controller which stores instructions for applying pattern recognition algorithms.

Five authentic (Authentic) urine specimens were obtained from adult volunteers, three male and two female. Five synthetic urine samples were purchased and prepared in accordance with the instructions provided. The brand names of the synthetic urine samples were marketed by their vendors under the names Synthetix5, Number 1, Quick Fix, Whizz Kit, and Monkey Whizz. In general, the instruction provided with each kit indicated that the purpose of the product was to mimic obtaining authentic urinary specimens at normal physiologic temperatures (98-100° F.). The synthetic urine samples were brought to physiological temperature by applying a heat pad to the urine bladder (or urine bottle as in the case of Quick Fix) included in the kits and strapping it to an individual with an elastic belt also, included with the kits. The individual's skin was the main source of heat in elevating the synthetic urine temperature. The synthetic urine was then placed in urine sample cups and tested as described below.

As the main component of both synthetic and authentic urines is water, three of the sensors within the electronic nose were deactivated because they are hydroxyl-group-specific. This was done to avoid saturating the sensors resulting in the creation of unduly influential data points.

The successful operation of the Cyranose 320 depends upon the samples and methodology used to train it. When introduced to an unknown vapor sample, the Cyranose 320 digitizes the sensor readings and compares the new digital image of the vapor to those stored in its memory during training.

The electronic nose was trained to recognize a chemical vapor in the headspace of each urine sample, authentic and synthetic, by introducing each headspace to the instrument according to manufacturer's instructions. A digital image of each vapor was created and stored within the controller in the electronic nose.

A baseline measurement was performed which served as a negative control. The baseline measurement sampled room air which did not include the headspace of any of the urine samples.

Each urine sample, authentic and synthetic, was sampled as an "unknown" sample by the electronic nose and the pattern recognition algorithms stored on the nontransitory computer readable medium within the controller were applied to the sensor measurements. Specifically, headspace samples from both synthetic and authentic urine samples which were open to the atmosphere were taken with a sampling time of 60 seconds each. Six to ten replicate samples of the headspace of each synthetic urine sample were analyzed as well as two from each authentic urine, the latter being limited by the instrument algorithms provided on the controller within the electronic nose. The results are tabulated in Tables 1-3 and illustrated in FIG. 3.

Upon introducing a sample in chemical in vapor form to the electronic nose, the sensors measure a change in resistance as $(R_{max}-R_0)/R_0$ where $R_0$ is the resistance measured during a baseline draw and $R_{max}$ is the maximum resistance measured induced by the chemical vapor. It is by comparing the change in resistance from all the sensors in tandem that the electronic nose differentiates between different compounds. The system was purged between samples to allow a reset of the sensors after sampling.

Results and Discussion:

Table 1 lists the samples that were introduced to the electronic nose as part of training in the column labeled "Class." The sums of the numbers in each data row represent the total number of samples that were presented for each individual class. Upon presenting all the samples to the electronic nose, the collected data were then compared to the stored profiles from each class of synthetic urine obtained during training using classification algorithms stored on the controller within the electronic nose. These algorithms determine which class the digital profile of each sample best matches. The numbers in the data columns represent the number of times each sample best matched the stored pattern for each class. For example, Synthetix5 has a total of 9 samples (sum of numbers in the first data row), 8 of which were identified correctly and 1 of which was misidentified as Quick Fix.; Monkey Whizz has a total of 10 samples (sum of numbers in the fifth data row), 8 of which were identified correctly, 1 being misidentified as Whizz Kit, and 1 being misidentified as Authentic. The numbers for correct predictions are presented in bold.

TABLE 1

Cross-Validation Results of Synthetic and Authentic Urine Samples.

| | | Identified As | | | | | |
|---|---|---|---|---|---|---|---|
| | Class | Synthetix5 | Number 1 | Quick Fix | Whizz Kit | Monkey Whizz | Authentic |
| Trained As | Synthetix5 | 8 | 0 | 1 | 0 | 0 | 0 |
| | Number 1 | 0 | 6 | 0 | 0 | 0 | 0 |
| | Quick Fix | 2 | 0 | 8 | 0 | 0 | 0 |

TABLE 1-continued

Cross-Validation Results of Synthetic and Authentic Urine Samples.

| | | | Identified As | | | |
|---|---|---|---|---|---|---|
| Class | Synthetix5 | Number 1 | Quick Fix | Whizz Kit | Monkey Whizz | Authentic |
| Whizz Kit | 0 | 0 | 0 | 6 | 2 | 0 |
| Monkey Whizz | 0 | 0 | 0 | 1 | 8 | 1 |
| Authentic | 0 | 0 | 0 | 0 | 1 | 9 |

Referring now to Table, 2, the data in the column labeled Overall Percentage indicates the ability of the electronic nose to differentiate between each of the six classes (five synthetic and one authentic). The data in the column labeled Authentic Specification indicates the ability of the electronic nose to differentiate between synthetic and authentic urine. The percentage in the Authentic Specification column was calculated by combining all the synthetic urines into a single class and authentic urine samples into a different single class. Referencing Table 1, it is noted that only 1 of the synthetic urine samples was misidentified as authentic and 1 authentic urine sample was misidentified as synthetic. This results in 2 of the 53 (3.774%) samples incorrectly differentiated and 51 of the 53 (96.226%) samples correctly differentiated as synthetic or authentic specimens.

TABLE 2

Summary Statistics.

| | Overall Percentage | Authentic Specification |
|---|---|---|
| Correct | 84.906% | 96.226% |
| Incorrect | 15.094% | 3.774% |

Figure 3:
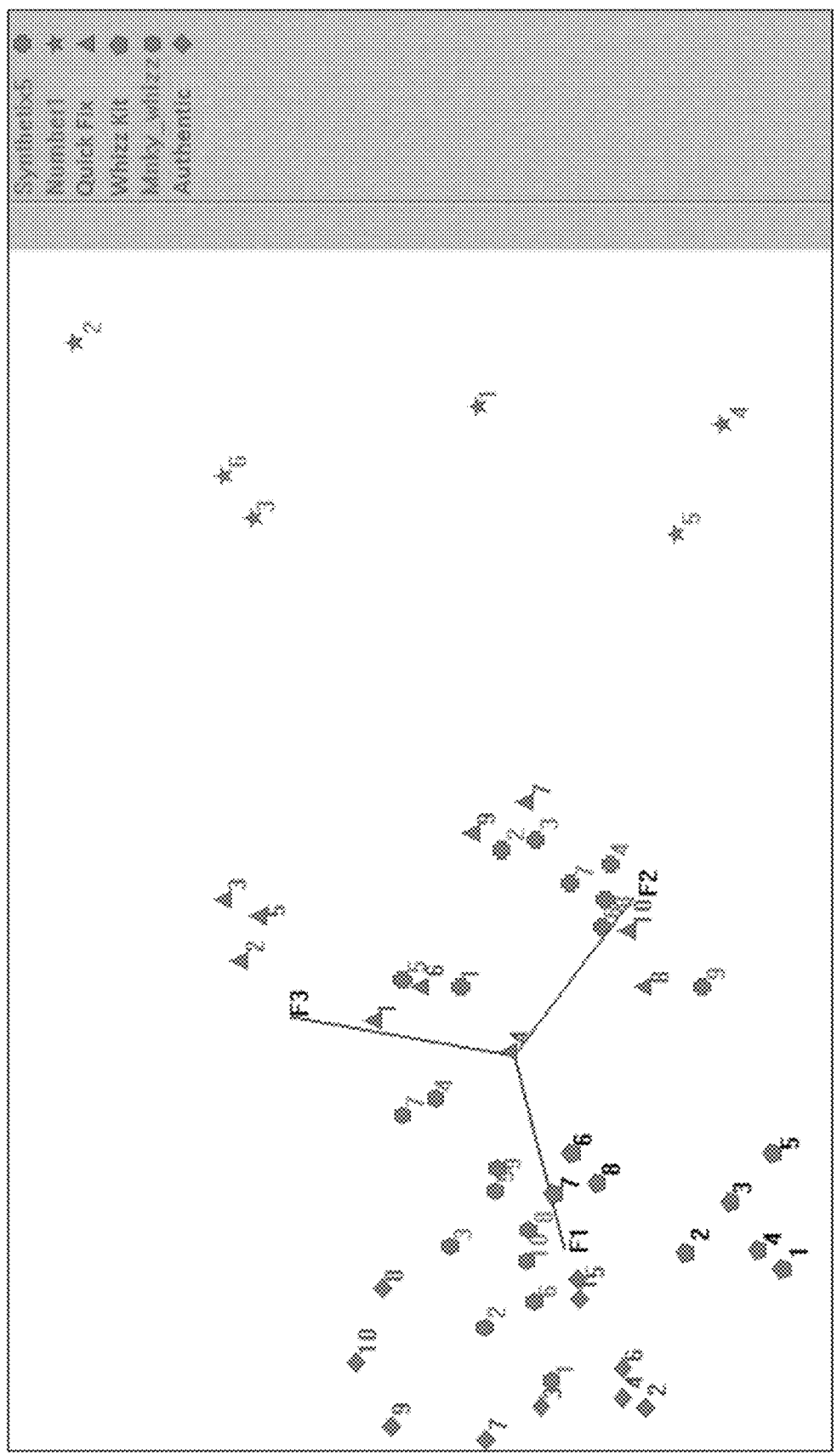
FIG. 3 is a principal component analysis projection plot of synthetic and authentic urine samples assayed using a handheld resistor array.

FIG. 3 shows a principal component analysis projection plot of data collected by the hand-held electronic nose when analyzing synthetic and authentic urine samples. The experiment was conducted as described above. The electronic nose was trained on all five synthetic urine samples shown in the plot and a single authentic urine sample. A striking feature illustrated in the FIG. 3 is how dispersed each of the samples are relative to each other. It is also notable how far distanced the synthetic urine brand Number 1 is from the other synthetic urines. Synthetic urine brand Number 1 is farthest from the authentic urines in Euclidian space, resulting in a low probability of it being misidentified as another brand or even as an authentic urinary specimen. In agreement, the data in Table 1 indicates that none of the Number 1 samples was identified as another synthetic brand nor as authentic urine.

The two classes that were closest together in Euclidian space were the two synthetic brands Whizz Kit and Monkey Whizz. In agreement, the data shown in Table 1 indicates that two out of the eight Whizz Kit samples were misidentified as Monkey Whizz samples. Similarly, the next two closest classes in Euclidian space were the synthetic brands Quick Fix and Synthetix5. The data shown in Table 1 indicates that one of the nine Syenthetix5 samples was misidentified as a Quick Fix sample. As noted in Table 2, the overall accuracy is about 85%. FIG. 3 further supports the interpretation that the electronic nose is capable, not only of distinguishing between authentic and synthetic urine samples, but between synthetic urine samples with different formulations.

Table 3 provides the Euclidian distances plotted in FIG. 3 in numerical form. We note that the Euclidian distances of the authentic samples from the synthetic brands Synthetix5, Number 1 and Quick Fix are substantial and hence the probability for misidentification is low. This notion is supported by the data in Table 1 where none of these three synthetic urine samples was identified as an authentic specimen and vice versa. However, we note that the distances between the authentic urine specimens and each of the synthetic brands Whizz Kit and Monkey Whizz are somewhat close to each other, being 3.423 and 3.082 respectively (see Table 3). The benchmark minimum value is 5. Referring again to Table 1, it may be noted that only one of the ten Monkey Whizz samples was misidentified as an authentic sample and only one of the ten authentic samples was misidentified as a Monkey Whizz sample. Each of the two synthetic urines, Whizz Kit and Monkey Whizz, were correctly identified as synthetic with approximately 90% accuracy. If we reframe the data and combine all the synthetic data into a single class and keep the authentic data as-is, we see that authentic urine samples were misidentified as synthetic urine only twice, leading to a 96% accuracy for the "authentic specification statistic" listed in Table 2. Such a scenario might be encountered in a mandatory drug test where individuals are randomly chosen to submit a urinary specimen for testing with the question to address being, "Is this specimen authentic?" Our results indicate that there is a 96% chance of answering the question correctly.

TABLE 3

Interclass Euclidean Distances.

| Class | Synthetix5 | Number 1 | Quick Fix | Whizz Kit | Monkey Whizz | Authentic |
|---|---|---|---|---|---|---|
| Synthetix5 | | 9.649 | 2.267 | 4.454 | 5.337 | 7.751 |
| Number 1 | | | 9.412 | 13.241 | 13.682 | 15.710 |
| Quick Fix | | | | 5.536 | 5.879 | 8.516 |
| Whizz Kit | | | | | 1.784 | 3.423 |
| Monkey Whizz | | | | | | 3.082 |
| Authentic | | | | | | |

Table 4 below illustrates a use of the method to identify synthetic urine on which the electronic nose has not been trained. This experiment was designed to replicate an environment in which individuals periodically provide a urine sample for testing. For example, the environment may be a treatment facility for drug addiction and the urine samples are tested as part of the recovery program. In such an environment, individuals who have used illicit drugs and who wish to avoid detection may present a synthetic urine sample obtained from one of many vendors. It is unlikely that the electronic nose will have been trained on every available synthetic urine. Therefore, we asked if the electronic nose can identify a synthetic urine formulation on which it has not been trained.

In this experiment, the unknown synthetic urine was supplied as a vial of dry, powdered synthetic urine. It was obtained from the manufacturer of the Whizz Kit synthetic urine and sold under the trade name Golden Shower. This product was designated for use with a bladder which a user fills with the reconstituted synthetic urine. The user then straps the bladder to his/her body to warm the synthetic urine to body temperature with the assistance of a hand warmer.

Following the instructions provided, the powder was reconstituted with bottled water and introduced into the bladder provided by the manufacturer. The filled bladder was then strapped onto a test subject's body and a hand warmer placed in contact with the bladder until physiologic temperature was achieved. Four individuals participated in the experiment, each wearing a filled bladder and providing samples of the unknown synthetic urine, Golden Shower. Ten replicate headspace samples were obtained from each individual. The entries in the Overall Class Assignment column indicate whether the electronic nose identified the Golden Shower sample as authentic or synthetic urine. The entries in the Specific Class Assignment column indicate the identity the electronic nose assigned to each sample. The identity was selected from either authentic urine or one of the synthetic urine formulations on which the electronic nose was trained (which did not include Golden Shower). In those cases where two synthetic urines are listed, the instrumental algorithm could not differentiate between the two identities.

TABLE 4

Results Obtained by Analyzing an Unknown Synthetic Urine against Individual Donors.

| Test Subject Identification | Synthetic Urine | Overall Class Assignment | Specific Class Assignment |
|---|---|---|---|
| Waqmw1 | Golden Shower | Synthetic Urine | Quick Fix |
| | | Synthetic Urine | Quick Fix |
| | | Synthetic Urine | Monkey Whizz |
| | | Synthetic Urine | Quick Fix |
| | | Synthetic Urine | Quick Fix |
| | | Synthetic Urine | Whizz Kit |
| | | Synthetic Urine | Quick Fix |
| | | Synthetic Urine | Quick Fix |
| | | Synthetic Urine | Quick Fix/ Monkey Whizz |
| | | Synthetic Urine | Quick Fix |
| Yiipw1 | Golden Shower | Synthetic Urine | Whizz Kit |
| | | Synthetic Urine | Monkey Whizz/ Synthetix5 |
| | | Synthetic Urine | Whizz Kit |
| | | Authentic Urine | ************ |
| | | Undecided | ************ |
| | | Synthetic Urine | Monkey Whizz |
| | | Synthetic Urine | Whizz Kit |
| | | Undecided | ************ |
| | | Authentic Urine | ************ |
| | | Synthetic Urine | Monkey Whizz |
| Yfkkm1 | Golden Shower | Synthetic Urine | Quick Fix/Synthetix5 |
| | | Synthetic Urine | Quick Fix |
| | | Synthetic Urine | Quick Fix |
| | | Synthetic Urine | Whizz Kit |
| | | Synthetic Urine | Monkey Whizz |
| | | Synthetic Urine | Monkey Whizz |
| | | Synthetic Urine | Whizz Kit |
| | | Synthetic Urine | Whizz Kit |
| | | Synthetic Urine | Whizz Kit |
| | | Synthetic Urine | Monkey Whizz/ Whizz Kit |

TABLE 4-continued

Results Obtained by Analyzing an Unknown Synthetic Urine against Individual Donors.

| Test Subject Identification | Synthetic Urine | Overall Class Assignment | Specific Class Assignment |
|---|---|---|---|
| Fkpwy | Golden Shower | Synthetic Urine | Whizz Kit |
| | | Synthetic Urine | Monkey Whizz |
| | | Synthetic Urine | Whizz Kit |
| | | Synthetic Urine | Monkey Whizz/ Whizz Kit |
| | | Synthetic Urine | Monkey Whizz |
| | | Synthetic Urine | Monkey Whizz |
| | | Synthetic Urine | Monkey Whizz |
| | | Synthetic Urine | Monkey Whizz/ Whizz Kit |
| | | Synthetic Urine | Monkey Whizz |
| | | Synthetic Urine | Monkey Whizz/ Whizz Kit |

As illustrated in Table 4, for three out of the four test subjects who participated in the experiment, all ten Golden Shower replicates were predicted to be a type of synthetic urine selected from the four classes on which the electronic nose had been trained. Because the test sample was a fifth type of synthetic urine on which the electronic nose had not been trained, these predictions are obviously not correct. However, the overall class to which the specific class assignment resides, that being the synthetic urines as listed in the third column, were all correct. An exception was found in the second participant identified as Yiipu1, where six of the replicates were assigned to the correct overall class (Synthetic Urine), two of the replicates were assigned incorrectly to the Authentic Urine overall class, and two replicates were undecided.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A method for differentiating authentic from synthetic urine comprising the steps of:
    providing an electronic volatile compound sensing device, the device comprising:
        a vapor sampling system;
        an array of resistive microchemical sensors;
        wherein the array of resistive microchemical sensors further comprise at least one hydroxylgroup-specific resistive microchemical sensor that may be activated and deactivated during testing;
        a controller, the controller comprising nontransitory computer readable medium which stores at least one algorithm, wherein at least one of the at least one algorithm comprises instructions to recognize patterns in changes in resistance at each of the resistive microchemical sensors;

training the device to a synthetic urine by:
introducing the vapor sampling system to a vapor sample derived from a synthetic urine sample;
performing a measurement of a change in resistance at each of the resistive microchemical sensors in the array in response to the vapor sample derived from the synthetic sample; and
storing a pattern of change in resistance of each of the resistive microchemical sensors in response to the vapor sample derived from the synthetic urine sample in the controller;

training the device to authentic urine by:
introducing the vapor sampling system to a vapor sample derived from an authentic urine sample;
performing a measurement of a change in resistance at each of the resistive microchemical sensors in the array in response to the vapor sample derived from the authentic sample; and
storing a pattern of change in resistance of each of the resistive microchemical sensors in response to the vapor sample derived from the authentic urine sample in the controller;

conducting a measurement of a urine sample of unknown authenticity comprising the steps of:
introducing the vapor sampling system to a vapor sample derived from a urine sample of unknown authenticity;
performing a measurement of a change in resistance at each of the resistive microchemical sensors in the array in response to the vapor sample derived from the urine sample of unknown authenticity; and
storing a pattern of change in resistance of each of the resistive microchemical sensors in response to the vapor sample derived from the authentic urine sample in the controller; and comparing, by the controller, the stored pattern from the sample of unknown authenticity to the stored patterns from the patterns from the synthetic urine and from the sample from the authentic urine to differentiate the sample of unknown authenticity from the synthetic urine or from the authentic urine.

2. The method of claim 1, further comprising the step of conducting a baseline measurement, the baseline measurement comprising the steps of:
introducing the vapor sampling system to an air sample comprising a negative control sample;
performing a measurement of a change in resistance at each of the resistive microchemical sensors in the array in response to the air sample comprising the negative control sample; and
storing a pattern of change in resistance of each of the resistive microchemical sensors in response to the air sample comprising the negative control sample.

3. The method of claim 2, wherein the negative control sample comprises room air or water.

4. The method of claim 2, further comprising the step of performing a calculation to determine $R_{max}/R_o$, wherein $R_o$ represents the resistance measured by each of the resistive microchemical sensors in the array following the baseline measurement, and wherein $R_{max}$ represents a maximum resistance measured by each of the resistive microchemical sensors in the array after introducing the device to the vapor sample derived from the urine sample of unknown authenticity.

5. The method of claim 1, further comprising the step of providing an output, the output comprising an analysis of the authenticity of the urine sample of unknown authenticity.

6. The method of claim 5, wherein the output comprises a statistical analysis of the analysis of the authenticity of the urine sample of unknown authenticity.

7. The method of claim 1, wherein the array of resistive microchemical sensors consists of one or more sensors from the following list: metal oxide semiconductors, conducting polymers, piezoelectric sensors, and metal oxide sensors.

8. The method of claim 1, wherein the at least one algorithm comprises a classification algorithm comprising instructions for performing one or more of the following analyses: a multivariate statistical procedure, a k-nearest neighbors prediction probability routine, a k-means cluster analysis, a categorical data analysis, a soft independent modeling of class analogy analysis, a single-class analysis, and a support vector machine analysis.

9. The method of claim 8, wherein the at least one algorithm comprises instructions to perform the multivariate statistical procedure comprising a principal component analysis.

10. The method of claim 1, further comprising deactivating the at least one hydroxylgroup-specific resistive microchemical sensor.

11. The method of claim 1, wherein the synthetic urine sample and the authentic urine sample are between approximately 970 F and approximately 1040 F.

12. The method of claim 1, comprising the step of training the device to a plurality of synthetic urine samples and a plurality of authentic urine samples.

13. The method of claim 1, wherein the array comprises at least 20 resistive microchemical sensors.

14. The method of claim 1, wherein the device is handheld.

15. The method of claim 1, wherein the device is installed in a toilet.

16. The method of claim 15, wherein the toilet comprises a toilet bowl, and wherein the device is in communication with a fan configured to drive a headspace from the toilet bowl toward the device.

17. The method of claim 16, wherein the fan is configured to drive the headspace from the toilet bowl in a plurality of velocities, and further comprising the step of adjusting the fan to drive the headspace from the toilet at a desired velocity.

18. The method of claim 15, wherein the toilet comprises a P-trap and an air pipe.

19. The method of claim 18, wherein the air pipe comprises a valve configured to regulate the entry of the headspace of the toilet bowl into the air pipe.

20. The method of claim 15, wherein the toilet is a medical toilet.

* * * * *